(12) United States Patent
Bizup

(10) Patent No.: US 9,504,815 B2
(45) Date of Patent: Nov. 29, 2016

(54) LOW PROFILE VENOUS ACCESS PORT ASSEMBLY

(75) Inventor: Raymond Bizup, Feasterville, PA (US)

(73) Assignee: Medical Components, Inc., Harleysville, PA (US)

( * ) Notice: Subject to any disclaimer, the term of this patent is extended or adjusted under 35 U.S.C. 154(b) by 1104 days.

(21) Appl. No.: 12/144,171

(22) Filed: Jun. 23, 2008

(65) Prior Publication Data

US 2008/0319405 A1    Dec. 25, 2008

Related U.S. Application Data

(60) Provisional application No. 60/936,849, filed on Jun. 22, 2007.

(51) Int. Cl.
| | | |
|---|---|---|
| *A61M 39/02* | (2006.01) | |
| *A61M 39/00* | (2006.01) | |
| *A61M 39/10* | (2006.01) | |

(52) U.S. Cl.
CPC ......... *A61M 39/0208* (2013.01); *A61M 39/02* (2013.01); *A61M 2039/0063* (2013.01); *A61M 2039/0072* (2013.01); *A61M 2039/027* (2013.01); *A61M 2039/0223* (2013.01); *A61M 2039/0229* (2013.01); *A61M 2039/1072* (2013.01)

(58) Field of Classification Search
CPC ............ A61M 2039/0229; A61M 2039/0063; A61M 2039/0072; A61M 2039/027; A61M 2039/1072; A61M 39/02; A61M 39/0208; A61M 39/0247; A61M 39/04
USPC ....................................... 604/288.01-288.04
See application file for complete search history.

(56) References Cited

U.S. PATENT DOCUMENTS

| | | |
|---|---|---|
| D44,302 S | 7/1913 | Director |
| D130,852 S | 12/1941 | Rothschild |
| 4,559,043 A | 12/1985 | Whitehouse et al. |

(Continued)

FOREIGN PATENT DOCUMENTS

| | | |
|---|---|---|
| EP | 1 520 541 A1 | 4/2005 |
| EP | 1 736 196 A2 | 12/2006 |

(Continued)

OTHER PUBLICATIONS

PCT/US08/67657—International Preliminary Report on Patentability—Dated Nov. 2, 2009 (7 Pages).
International Search Report dated Sep. 19, 2008; PCT/US08/067657 (3 pages).
Written Opinion dated Sep. 19, 2008; PCT/US08/067657 (5 pages).
EP Application No. 08 771 585.0, Communication, dated Jul. 16, 2010, 4 pages.
EP Application No. 08 771 585.0, Reply, dated Nov. 25, 2010, 10 pages.

(Continued)

*Primary Examiner* — Imani Hayman
*Assistant Examiner* — Jenna Zhang
(74) *Attorney, Agent, or Firm* — Buchanan Ingersoll & Rooney

(57) ABSTRACT

A venous access port assembly having a housing base with a discharge stem, a septum, and a cap. An interior reservoir is defined by a well in the housing base and the bottom surface of the septum, and a passageway extends from the reservoir through the discharge stem. The cap is secured to the housing base and securely retains the septum in the assembly, compressing an annular flange of the septum against a septum seat of the housing base. Horizontal ribs on the interior of the cap snap into complementary grooves on the side wall of the housing base to mechanically lock together the cap and housing base during curing of the solvent bonding agent. The cap is mechanically secured and bonded to the housing base. Crush ribs on the interior surface of the cap, precisely center the cap about the housing base during assembly and compensating for manufacturing tolerances.

20 Claims, 2 Drawing Sheets

(56) References Cited

U.S. PATENT DOCUMENTS

| | | |
|---|---|---|
| 4,673,394 A | 6/1987 | Fenton, Jr. et al. |
| 4,681,560 A | 7/1987 | Schulte et al. |
| 4,692,146 A | 9/1987 | Hilger |
| 4,695,273 A | 9/1987 | Brown |
| 4,704,103 A | 11/1987 | Stoeber et al. |
| 4,710,167 A | 12/1987 | Lazorthes |
| 4,762,517 A | 8/1988 | McIntyre et al. |
| 4,772,270 A | 9/1988 | Wiita et al. |
| 4,778,452 A | 10/1988 | Moden et al. |
| 4,781,680 A | 11/1988 | Redmond et al. |
| 4,802,885 A | 2/1989 | Weeks et al. |
| 4,886,501 A | 12/1989 | Johnston et al. |
| 4,892,518 A | 1/1990 | Cupp et al. |
| 4,904,241 A | 2/1990 | Bark |
| 4,915,690 A | 4/1990 | Cone et al. |
| 5,013,298 A | 5/1991 | Moden et al. |
| 5,045,060 A | 9/1991 | Melsky et al. |
| 5,084,015 A | 1/1992 | Moriuchi |
| 5,108,377 A | 4/1992 | Cone et al. |
| 5,137,529 A | 8/1992 | Watson et al. |
| 5,167,629 A | 12/1992 | Vertenstein et al. |
| 5,167,638 A | 12/1992 | Felix et al. |
| 5,180,365 A | 1/1993 | Ensminger et al. |
| 5,185,003 A | 2/1993 | Brethauer |
| 5,199,948 A | 4/1993 | McPhee |
| 5,207,644 A | 5/1993 | Strecker |
| 5,213,574 A | 5/1993 | Tucker |
| 5,263,930 A | 11/1993 | Ensminger |
| D342,134 S | 12/1993 | Mongeon |
| 5,281,199 A | 1/1994 | Ensminger et al. |
| 5,281,205 A | 1/1994 | McPherson |
| 5,318,545 A | 6/1994 | Tucker |
| 5,356,381 A | 10/1994 | Ensminger et al. |
| 5,360,407 A | 11/1994 | Leonard |
| 5,387,192 A * | 2/1995 | Glantz et al. ............. 604/288.02 |
| 5,399,168 A | 3/1995 | Wadsworth, Jr. et al. |
| 5,476,460 A | 12/1995 | Montalvo |
| 5,503,630 A | 4/1996 | Ensminger et al. |
| 5,556,381 A | 9/1996 | Ensminger et al. |
| 5,558,641 A * | 9/1996 | Glantz ............... A61M 39/0208 604/175 |
| 5,562,617 A | 10/1996 | Finch, Jr. et al. |
| 5,593,028 A | 1/1997 | Haber et al. |
| 5,607,393 A | 3/1997 | Ensminger et al. |
| 5,613,945 A | 3/1997 | Cai et al. |
| 5,620,419 A | 4/1997 | Lui et al. |
| 5,637,102 A | 6/1997 | Tolkoff et al. |
| 5,713,858 A | 2/1998 | Heruth et al. |
| 5,718,682 A | 2/1998 | Tucker |
| 5,743,873 A | 4/1998 | Cai et al. |
| 5,792,104 A | 8/1998 | Speckman et al. |
| 5,833,654 A | 11/1998 | Powers et al. |
| 5,848,989 A | 12/1998 | Villani |
| 5,951,512 A | 9/1999 | Dalton |
| 5,989,216 A * | 11/1999 | Johnson ............ A61M 39/0208 604/175 |
| 6,086,555 A | 7/2000 | Eliasen et al. |
| 6,090,066 A | 7/2000 | Schnell |
| 6,113,572 A | 9/2000 | Gailey et al. |
| 6,190,352 B1 | 2/2001 | Haarala et al. |
| 6,213,973 B1 | 4/2001 | Eliasen et al. |
| 6,503,228 B1 | 1/2003 | Li et al. |
| 6,527,754 B1 * | 3/2003 | Tallarida ............ A61M 39/0208 604/288.02 |
| 6,562,023 B1 | 5/2003 | Marrs et al. |
| D480,942 S | 10/2003 | Ishida et al. |
| 6,719,739 B2 | 4/2004 | Verbeek et al. |
| 6,758,841 B2 | 7/2004 | Haarala et al. |
| D498,894 S | 11/2004 | Gould |
| 6,878,137 B2 | 4/2005 | Benchetrit |
| 6,971,390 B1 | 12/2005 | Vasek et al. |
| 6,997,914 B2 | 2/2006 | Smith et al. |
| D518,573 S | 4/2006 | French |
| 7,186,236 B2 | 3/2007 | Gibson et al. |
| D546,440 S | 7/2007 | Burnside |
| D556,153 S | 11/2007 | Burnside |
| D562,443 S | 2/2008 | Zinn et al. |
| D574,950 S | 8/2008 | Zawacki et al. |
| 7,628,776 B2 * | 12/2009 | Gibson ............ A61M 5/14276 604/288.01 |
| 7,651,483 B2 * | 1/2010 | Byrum et al. ........... 604/288.01 |
| 2004/0006316 A1 | 1/2004 | Patton |
| 2004/0204692 A1 * | 10/2004 | Eliasen ............. A61M 39/0208 604/288.02 |
| 2004/0204962 A1 * | 10/2004 | Howser et al. ................... 705/2 |
| 2005/0077688 A1 * | 4/2005 | Voegele ............ A61B 17/3462 277/628 |
| 2005/0085778 A1 | 4/2005 | Parks |
| 2005/0159717 A1 * | 7/2005 | Holtermann ......... A61F 5/4407 604/332 |
| 2005/0171502 A1 | 8/2005 | Daly et al. |
| 2005/0283119 A1 * | 12/2005 | Uth ................... A61M 39/0208 604/175 |
| 2006/0100592 A1 | 5/2006 | Eliasen |
| 2006/0116648 A1 | 6/2006 | Hamatake |
| 2006/0184141 A1 | 8/2006 | Smith et al. |
| 2006/0184142 A1 | 8/2006 | Schon et al. |
| 2006/0217659 A1 | 9/2006 | Patton |
| 2006/0217668 A1 | 9/2006 | Schulze et al. |
| 2006/0224129 A1 | 10/2006 | Beasley et al. |
| 2006/0247584 A1 | 11/2006 | Sheetz et al. |
| 2006/0264898 A1 | 11/2006 | Beasley et al. |
| 2007/0010790 A1 * | 1/2007 | Byrum ............. A61M 39/0208 604/288.02 |
| 2007/0078391 A1 | 4/2007 | Wortley et al. |
| 2007/0078416 A1 | 4/2007 | Eliasen |
| 2007/0149947 A1 * | 6/2007 | Byrum ............. A61M 39/0208 604/508 |
| 2007/0185462 A1 | 8/2007 | Byrum |
| 2007/0219510 A1 | 9/2007 | Zinn et al. |
| 2007/0233017 A1 | 10/2007 | Zinn et al. |
| 2007/0255226 A1 | 11/2007 | Tennican et al. |
| 2007/0270770 A1 | 11/2007 | Bizup |
| 2007/0276344 A1 | 11/2007 | Bizup |
| 2008/0140025 A1 | 6/2008 | Sheetz et al. |
| 2008/0319398 A1 | 12/2008 | Bizup |

FOREIGN PATENT DOCUMENTS

| | | |
|---|---|---|
| JP | 63-38535 | 3/1988 |
| JP | 2004/350937 | 12/2004 |
| JP | 2004-350937 | 12/2004 |
| JP | 2004350937 A * | 12/2004 |
| WO | 94/05351 | 3/1994 |
| WO | 97/01370 A1 | 1/1997 |
| WO | WO 97/01370 | 1/1997 |
| WO | 98/55167 | 12/1998 |
| WO | 99/34859 A1 | 7/1999 |
| WO | 2006/116438 A2 | 11/2006 |

OTHER PUBLICATIONS

EP Application No. 08 771 585.0, Communication, dated Dec. 28, 2011, 6 pages.

CN Application No. 200880021187.6, Office Action dated Jul. 26, 2011, 5 pages with 6-page translation.

EP Application No. 08 771 585.0-1526, Communication, dated Jun. 4, 2012, 6 pages.

PCT Application No. US/2007/011015, International Search Report, dated Jun. 10, 2008, 1 page.

PCT Application No. US/2007/011015, Written Opinion, dated Jun. 10, 2008, 3 pages.

PCT Application No. US/2007/011015, International Preliminary Report on Patentability, dated Nov. 23, 2009, 9 pages.

EP Application No. 07 794 615.0-2320, Extended European Search Report, dated Aug. 30, 2012, 6 pages.

JP 2010-513443, Office Action, dated Nov. 8, 2012, 4 pages.

* cited by examiner

LOW PROFILE VENOUS ACCESS PORT ASSEMBLY

CROSS-REFERENCE TO RELATED APPLICATIONS

This application claims priority from U.S. Provisional Patent Application Ser. No. 60/936,849 filed Jun. 22, 2007.

FIELD OF THE INVENTION

This relates to the field of medical devices and more particularly to catheter assemblies and ports therefor, for the infusion of fluids into the patient and withdrawal of fluids from the patient.

BACKGROUND OF THE INVENTION

Infusion ports for the infusion and/or withdrawal of fluids from a patient are well-known, secured to the proximal end of an implanted catheter. These ports are typically used for drug infusion or small amounts of blood withdrawal, where large flows of fluid are not required. The ports are assemblies of a needle-impenetrable housing with a discharge port in fluid communication with the catheter and the reservoir within the port housing, and provide a subcutaneous self-sealing septum that defines an access site for multiple needle sticks through the covering skin tissue of the patient, through the septum and into the reservoir, without the need to continuously search for new access sites. Examples of such ports are disclosed, for example, in U.S. Pat. Nos. 4,704,103; 4,762,517; 4,778,452; 5,185,003; 5,213,574 and 5,637,102.

It is desired to provide a venous access port assembly that is assuredly secured together in an assuredly sealed manner.

BRIEF SUMMARY OF THE INVENTION

The present invention is a venous access port having a housing and a septum, providing an interior reservoir and a passageway extending from the reservoir through a stem of a discharge port to establish fluid communication with a proximal end of a catheter lumen to which the port assembly is secured prior to placement of the assembly into a patient. The housing includes a base and a cap that together cooperate to secure a needle-penetrable septum within the assembly by compressing a seating flange of the septum in a seat of the housing base. The cap is mechanically secured to the housing base by a mechanical joint, preferably a retention rib of one of the housing base and cap extending radially outwardly to be received into a retention groove along the inside surface of the other of the housing base and cap in a snap fit, extending around most of the circumference of the port assembly. Preferably, solvent bonding is also provided between adjacent surfaces of the housing base and cap. The cap and housing base and septum are reduced in height from conventional ports to define a low profile venous access port assembly.

In a preferred embodiment of the present invention, a pair of horizontal retention ribs are defined on the cap's interior surface, a complementary pair of retention grooves are defined on the housing base's exterior surface. Due to manufacturing tolerances, a certain incremental "play" or gapping occurs between the facing surfaces of the cap and the housing base, and a plurality of crush ribs are provided along the interior surfaces of the cap, oriented vertically which minimize the effects of this "play." During assembly of the cap to the housing base, the outer surface of the housing base crushes the crush ribs during the very final stages of the mechanical securing process; but the crush ribs serve to precisely center the housing base within the cap are within the incremental "play" or gapping. Just prior to mechanical assembly, solvent is applied to several selected surfaces of the housing base exterior and the cap's interior, and the crush ribs facilitate solvent wicking to the surfaces of the interface, resulting in a superior bond between the cap and the housing base.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
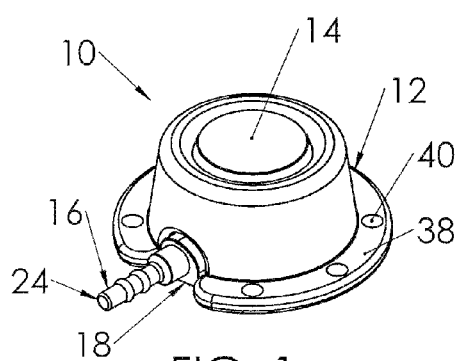
FIGS. 1 to 3 are isometric, elevation and top views of the venous access port of the present invention.
Figure 2:
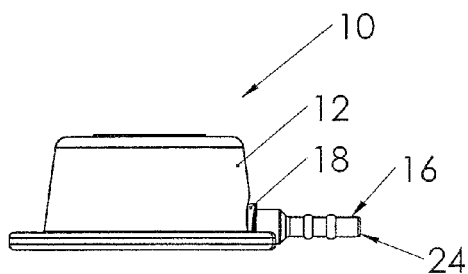
Figure 3:
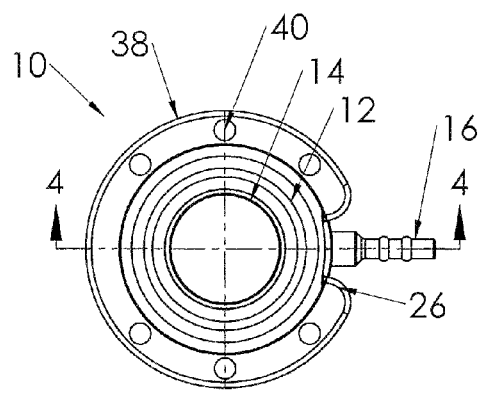

Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of FIGS. 1 to 4 includes a housing 12 and a septum 14, with a discharge stem 16 extending from a distal end 18 of the port assembly 10; discharge stem 16 is to be attached securely and sealingly to the proximal end of a catheter (not shown) such as by a locking sleeve or clamp (not shown). A passageway 20 extends from the interior reservoir 22 to the distal tip opening 24 of discharge stem 16, along the longitudinal port axis. A recess 26 is seen to be provided along both sides of discharge port 16, facilitating insertion of the discharge stem 16 into the catheter lumen and providing a clearance for a locking sleeve or clamp (not shown) utilized to compress the catheter lumen wall against the exterior surface of the discharge port 16 for assured sealed connection of the catheter with the port assembly 10.

Figure 4:
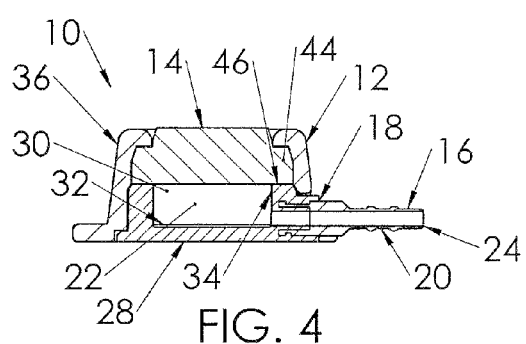
FIG. 4 is a longitudinal cross-section view of the port of FIG. 1 taken along lines 4-4 of FIG. 3.

With reference now to FIG. 4, the interior of the port assembly 10 is shown to provide an interior reservoir 22. Housing 12 is shown to include a housing base 28 of needle-impenetrable material that includes a well 30 having a bottom floor 32 and side walls 34 that define the interior reservoir 22 beneath septum 14. Cap 36 is securable to housing base 28 to, in turn, secure septum 14 in position in the port assembly 10. Cap 36 is described in greater particularity with respect to FIGS. 8 to 11. Cap 36 includes a base flange 38 extending radially outwardly from the bottom of well 30 of housing base 28, and base flange 38 includes openings 40 that serve to enable suturing to the patient upon placement of the venous access port and the attached catheter into the patient.

Figure 5:
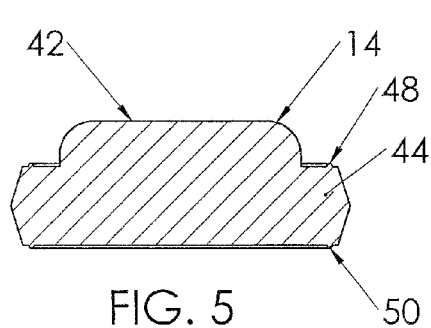
FIG. 5 is a cross-section views of the septum of FIGS. 1 to 4.

Septum 14 is shown in FIG. 5 and is seen to have a flattened top surface 42 and an annular seating flange 44. Seating flange 44 is disposed upon a flange seat of housing base 28, preferably under radially inward compression. Vertical compression of seating flange 44 is also attained when cap 36 is snapped onto housing base 28, compressing seating flange 44 against flange seat 46, as seen in FIG. 4. Also, seating flange 44 is seen to have rounded ridges 48,50 disposed on the upper and lower surfaces of seating flange 44 and extending completely around the septum, and are vertically co-aligned. The pair of rounded ridges 48,50 focuses greater compression circumferentially completely around the upper and lower surfaces of seating flange 44 upon assembly to assure sealing with respect to cap 36 and housing base 28, and sealing the reservoir 22.

Figure 6:
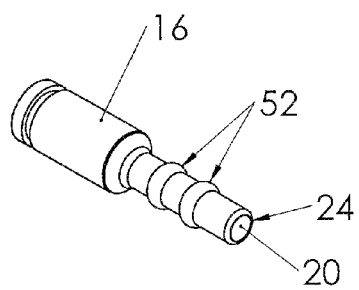
FIG. 6 is an enlarged isometric view of the discharge stem of the port of FIGS. 1 to 4.

In FIG. 6 is seen discharge stem 16 which comprises a discrete component such as of titanium metal, that is insert molded to housing base 28. Discharge stem 16 is shown to have a pair of axially spaced, annular, rounded, atraumatic ridges 52 that facilitate the mechanical connection of the catheter proximal end with the port assembly 10.

Figure 7:
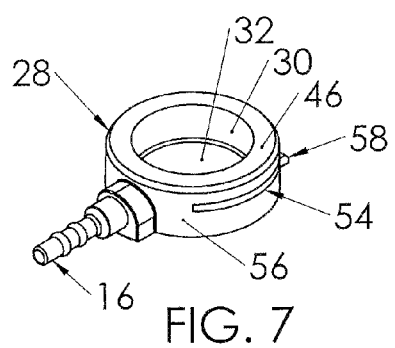

Housing base 28 is shown in FIG. 7 with discharge stem 16 already insert molded thereto. Its top surface is the flange seat 46 for septum flange 44. A pair of grooves 54 are defined into side surface 56 of housing base 28 on opposite sides thereof and comprise a first retention section of the mechanical snap-fit joint between the cap and the housing base upon assembly. Adjacent the bottom surface of the housing base, and on the side opposite the discharge stem 16 is a tab 58 that facilitates the appropriate orientation of the housing base to the cap during assembly, in cooperation with tab-receiving recess 60 of cap 36 (see FIGS. 9 and 10).

Cap 36 is illustrated in FIGS. 8 to 11 and includes a top portion 62 that is generously rounded and is preferably dimensioned to extend at least as high as the septum's top surface 42. Cap 36 also includes an annular side wall 64 that slopes downwardly and radially outwardly to skirt 38 adjacent cap bottom surface 66. Top portion 62 extends radially inwardly to cover seating flange 44 of septum 14 when assembled. An interior cavity 68 of cap 36 is shaped and dimensioned to receive thereinto both seating flange 44 of septum 14 and the upper portion of side wall 56 of housing base 28. Tab-receiving recess 60 is positioned opposite the distal opening for discharge stem 16, for receipt thereinto of tab 58 of the housing base to appropriately orient the housing base and the cap for optimum functioning of the mechanical fastening system described below.

A second retention section, a pair of retention ribs 70, is provided on the cap 36 around the greater part of the side surface of interior cavity 68 that corresponds with and is complementary to the first retention section or retention grooves 54 of housing base 28, discussed above with reference to FIG. 7. Retention ribs 70 and retention grooves 54 provide a snap fit, assuredly mechanically securing cap 36 to housing base 28. Preferably, retention ribs 70 may each have a radius of about 0.010 in (0.254 mm) and retention grooves 54 may have a radius of about 0.015 in (0.381 mm). Preferably, the retention ribs 70 of the cap comprise two coplanar horizontal portions equi-angularly spaced apart from each other, each extending circumferentially an angular distance between about 60° to 100° and more preferably between about 80° and 90° along the cap's interior surface; and the retention grooves 54 of the housing base 28 comprises two coplanar horizontal portions equi-angularly spaced apart from each other, each extending circumferentially an angular distance greater than that of the robs, and thus between about 70° to 110° and more preferably between about 85° to 95°.

A solvent bond is preferably formed between the facing surfaces of the septum, cap and housing base. The advantages of the mechanical retention of the cap to the housing base include assured securement of the cap and the housing base, in addition to the bonding thereof. Another advantage is more efficiency in the manufacturing of the venous access port assembly, and resultant economy: since the septum flange is under compression upon and after assembly, and since bonding is performed to further secure and seal the cap to the housing base, the mechanical lock holds the cap appropriately to the housing base while simultaneously maintaining appropriate compression of the septum flange, thus eliminating the necessity of tooling fixtures that otherwise would be needed to hold the three parts together until the bonding material fully cures.

Figure 8:
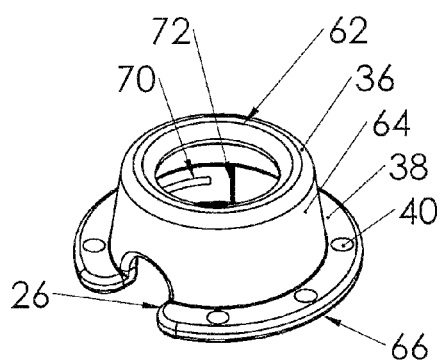
FIGS. 7 and 8 are isometric views of the housing base and the cap, respectively, of the venous access port of FIGS. 1 to 4.
Figure 9:
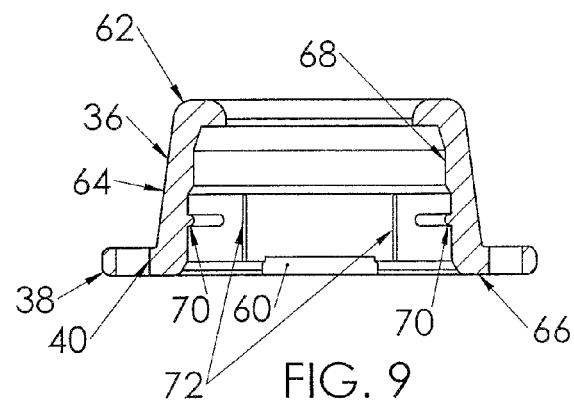
FIG. 9 is a transverse cross-sectional view of the cap of FIG. 8.
Figure 10:
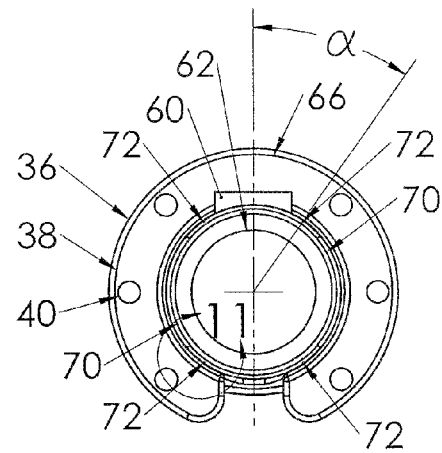
FIG. 10 is a bottom of the cap of FIGS. 8 and 9.

Referring in particular to FIGS. 8 to 10, the present invention further includes providing a centering system operating to precisely center the housing base 28 within interior cavity 68 of cap 36 when being fastened together during assembly. A plurality of vertical crush ribs 72 are defined on one of the housing base and the cap at the interface therebetween. Preferably, the crush ribs 72 are provided on the interior surface of cap 36 at angularly spaced locations thereabout, and further, preferably, crush ribs 72 are offset angularly from the retention ribs 70. During assembly of the housing base 28 to the cap 36, the exterior surface of the housing base becomes engaged with the crush ribs, and may compress the very small dimensioned ribs. The crush ribs of the present invention take up any looseness, slack or incremental "play" between the housing base and the cap due to manufacturing tolerances, and further improve the solvent bond by assuring an evenly circumferentially distributed incremental gap at the interface between the housing base and the cap facilitating maximum wicking of the solvent to adjacent surfaces at the interface.

Figure 11:
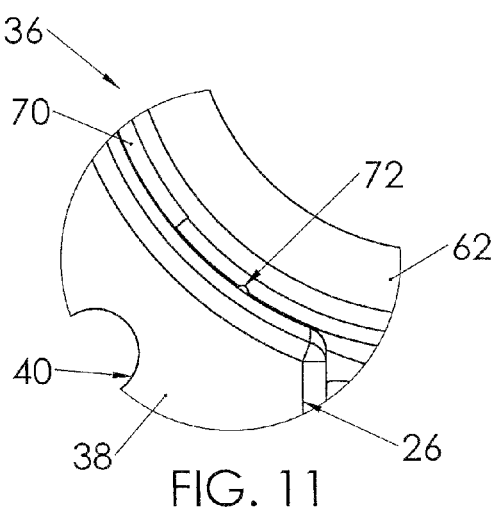
FIG. 11 is an enlarged view of a portion of the cap taken along lines 11-11 of FIG. 10.

In the described embodiment, the crush ribs 72 are each positioned at an angular distance $\alpha$ from the longitudinal port axis on either side, such as 35°, as seen in FIG. 10. As seen in FIG. 11, each crush rib may have a very small radius of about 0.005 in (0.127 mm). The solvent may be, for example, tetrahydrofuran, and beads thereof may be provided on selected surface portions of the cap and the housing base along the interface therebetween, including, for example, the outer periphery of top cap surface 46, the top of tab 58, the bottom portion of housing base side wall 56, and, after assembly, along the bottom surface of the assembly at the small cap/base interface gap.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A venous access port assembly, comprising:
a needle-penetrable septum comprising a flange having a circumference;
a housing comprising a housing base comprising an uppermost surface that is a septum seat onto which the septum is seated, the housing base further comprising a side wall comprising an exterior surface and a first retention section disposed circumferentially around a portion of the exterior surface;
a discharge port secured to the housing base, wherein a longitudinal port axis extends through the discharge port; and
a cap securable to the housing base for retaining the septum securely in the assembly, the cap comprising a side wall and an interior cavity, wherein an inwardly facing surface of the cap is associated and in contact with the exterior surface of the side wall of the housing base and the circumference of the flange of the septum, the cap further comprising a top portion extending radially inwardly to cover the flange of the septum, the cap further comprising a second retention section disposed circumferentially around a portion of the inwardly facing surface, the second retention section being associated with the first retention section and complementary thereto such that the first and second retention sections snap fit together to assure mechanical joining of the cap to the housing base thereby securing the septum in the housing,
wherein one of the housing base and the cap further comprises a plurality of angularly spaced vertical crush ribs on a surface thereof to be engaged by a surface of the other of the housing base and the cap for centering the housing base and the cap,
wherein one of the first and second retention sections comprises at least one retention rib and the other thereof comprises a complementary at least one retention groove,
wherein the at least one retention rib comprises two separate coplanar portions spaced apart from each other, each extending circumferentially an angular distance between about 60° to about 100°, and
wherein the at least one retention groove comprises two separate coplanar portions spaced apart from each other, each extending circumferentially an angular distance about 70° to about 110° and extending an angular distance greater than of the two separate coplanar portions of the at least one retention rib.

2. The venous access port assembly of claim 1, wherein the inwardly facing surface of the side wall of the cap and the exterior surface of the side wall of the housing base are solvent bonded to each other.

3. The venous access port assembly of claim 1, wherein the at least one retention groove is disposed on the exterior surface of the side wall of the housing base and the at least one retention rib is disposed on the inwardly facing surface of the side wall of the cap.

4. The venous access port assembly of claim 1, wherein the flange of the septum is seated onto the septum seat.

5. The venous access port assembly of claim 4, wherein the cap is configured to compress the flange of the septum.

6. The venous access port assembly of claim 1, wherein the first retention section comprises a retention rib having an arc length of at least 60° and between 60° and 100°, and the second retention section comprises a retention groove having an arch length greater than the arc length of the retention rib.

7. The venous access port assembly of claim 1, wherein the second retention section comprises a retention rib having an arc length of at least 60° and between 60° and 100°, and the first retention section comprises a retention groove having an arch length greater than the arc length of the retention rib.

8. The venous access port assembly of claim 1, wherein the plurality of angularly spaced vertical crush ribs are located about 35° from either side of the longitudinal port axis.

9. The venous access port assembly of claim 1, wherein the plurality of angularly spaced vertical crush ribs are disposed on the outer surface of the side wall of the base and are configured to be engaged by the inner surface of the side wall of the cap.

10. The venous access port assembly of claim 1, wherein the uppermost surface is substantially flat to receive the septum.

11. The venous access port assembly of claim 1, wherein the top portion of the cap has an inwardly facing surface associated with and in contact with a top surface of the flange of the septum.

12. A venous access port assembly, comprising:
a needle-penetrable septum comprising a flange having a circumference;
a housing comprising a housing base comprising an uppermost surface that is a septum seat onto which the septum is seated, the housing base further comprising a side wall comprising an exterior surface and a first retention section disposed circumferentially around a portion of the exterior surface;
a discharge port secured to the housing base, wherein a longitudinal port axis extends through the discharge port; and
a cap securable to the housing base for retaining the septum securely in the assembly, the cap comprising a side wall and an interior cavity, wherein an inwardly facing surface of the cap is associated and in contact with the exterior surface of the side wall of the housing base and the circumference of the flange of the septum, the cap further comprising a top portion extending radially inwardly to cover the flange of the septum, the cap further comprising a second retention section disposed circumferentially around a portion of the inwardly facing surface, the second retention section being associated with the first retention section and complementary thereto such that the first and second retention sections snap fit together to assure mechanical joining of the cap to the housing base thereby securing the septum in the housing,
wherein one of the housing base and the cap further comprises a plurality of angularly spaced vertical crush ribs on a surface thereof to be engaged by a surface of the other of the housing base and the cap for centering the housing base and the cap,
wherein one of the first and second retention sections comprises at least one retention rib and the other thereof comprises a complementary at least one retention groove,
wherein the at least one retention rib comprises two separate coplanar portions spaced apart from each other, each extending circumferentially an angular distance between about 80° to about 90°, and wherein the at least one retention groove comprises two separate coplanar portions spaced apart from each other, each extending circumferentially an angular distance about 85° to about 95° and extending an angular distance greater than of the two separate coplanar portions of the at least one retention rib.

13. The venous access port assembly of claim 12, wherein the inwardly facing surface of the side wall of the cap and the exterior surface of the side wall of the housing base are solvent bonded to each other.

14. The venous access port assembly of claim 12, wherein the at least one retention groove is disposed on the exterior surface of the side wall of the housing base and the at least one retention rib is disposed on the inwardly facing surface of the side wall of the cap.

15. The venous access port assembly of claim 12, wherein the plurality of angularly spaced vertical crush ribs are located about 35° from either side of the longitudinal port axis.

16. A venous access port assembly, comprising:
a needle-penetrable septum comprising a flange having a circumference;
a housing comprising a housing base comprising an uppermost surface that is a septum seat onto which the septum is seated, the housing base further comprising a side wall comprising an exterior surface and a first retention section disposed circumferentially around a portion of the exterior surface;
a discharge port secured to the housing base; and
a cap securable to the housing base for retaining the septum securely in the assembly, the cap comprising a side wall and an interior cavity, wherein an inwardly facing surface of the cap is associated and in contact with the exterior surface of the side wall of the housing base and the circumference of the flange of the septum, the cap further comprising a top portion extending radially inwardly to cover the flange of the septum, the cap further comprising a second retention section disposed circumferentially around a portion of the inwardly facing surface, the second retention section being associated with the first retention section and complementary thereto such that the first and second retention sections snap fit together to assure mechanical joining of the cap to the housing base thereby securing the septum in the housing,
wherein one of the housing base and the cap further comprises a plurality of angularly spaced vertical crush ribs on a surface thereof to be engaged by a surface of the other of the housing base and the cap for centering the housing base and the cap,
wherein one of the first and second retention sections comprises at least one retention rib and the other thereof comprises a complementary at least one retention groove,
wherein the at least one retention rib comprises two separate coplanar portions spaced apart from each other, each extending circumferentially an angular distance between about 60° to about 100°, and
wherein the at least one retention groove comprises two separate coplanar portions spaced apart from each other, each extending circumferentially an angular distance about 70° to about 110° and extending an angular distance greater than of the two separate coplanar portions of the at least one retention rib,
wherein the plurality of angularly spaced vertical crush ribs are angularly spaced offset from the at least one retention rib and from a longitudinal axis through the venous access port at least at the discharge port.

17. The venous access port assembly of claim 16, wherein the plurality of angularly spaced vertical crush ribs are located about 35° from either side of the longitudinal port axis.

18. The venous access port assembly of claim 16, wherein the plurality of angularly spaced vertical crush ribs have a radius of about 0.005 inches.

19. The venous access port assembly of claim 16, wherein the inwardly facing surface of the side wall of the cap and the exterior surface of the side wall of the housing base are solvent bonded to each other.

20. The venous access port assembly of claim 16, wherein the at least one retention groove is disposed on the exterior surface of the side wall of the housing base and the at least one retention rib is disposed on the inwardly facing surface of the side wall of the cap.

* * * * *